(12) United States Patent
Gyori

(10) Patent No.: US 12,246,001 B2
(45) Date of Patent: Mar. 11, 2025

(54) NON MEDICATED LOTION TO CORRECT ERECTILE DYSFUNCTION

(71) Applicant: Juliana Gyori, Crestline, CA (US)

(72) Inventor: Juliana Gyori, Crestline, CA (US)

( * ) Notice: Subject to any disclaimer, the term of this patent is extended or adjusted under 35 U.S.C. 154(b) by 0 days.

(21) Appl. No.: 17/842,652

(22) Filed: Jun. 16, 2022

(65) Prior Publication Data

US 2024/0058289 A1    Feb. 22, 2024

(51) Int. Cl.
| | | |
|---|---|---|
| *A61K 31/198* | (2006.01) | |
| *A61K 9/00* | (2006.01) | |
| *A61K 31/122* | (2006.01) | |
| *A61K 31/194* | (2006.01) | |
| *A61K 31/355* | (2006.01) | |
| *A61K 31/375* | (2006.01) | |
| *A61K 31/685* | (2006.01) | |
| *A61K 36/185* | (2006.01) | |
| *A61K 36/258* | (2006.01) | |
| *A61K 36/42* | (2006.01) | |
| *A61K 36/53* | (2006.01) | |
| *A61K 36/61* | (2006.01) | |
| *A61K 36/73* | (2006.01) | |
| *A61K 36/752* | (2006.01) | |
| *A61K 36/886* | (2006.01) | |
| *A61K 36/889* | (2006.01) | |
| *A61K 36/8905* | (2006.01) | |
| *A61K 36/8965* | (2006.01) | |
| *A61K 36/898* | (2006.01) | |
| *A61K 38/01* | (2006.01) | |
| *A61K 38/39* | (2006.01) | |

(52) U.S. Cl.
CPC .......... *A61K 31/198* (2013.01); *A61K 9/0034* (2013.01); *A61K 31/122* (2013.01); *A61K 31/194* (2013.01); *A61K 31/355* (2013.01); *A61K 31/375* (2013.01); *A61K 31/685* (2013.01); *A61K 36/185* (2013.01); *A61K 36/258* (2013.01); *A61K 36/42* (2013.01); *A61K 36/53* (2013.01); *A61K 36/61* (2013.01); *A61K 36/73* (2013.01); *A61K 36/752* (2013.01); *A61K 36/886* (2013.01); *A61K 36/889* (2013.01); *A61K 36/8905* (2013.01); *A61K 36/8965* (2013.01); *A61K 36/898* (2013.01); *A61K 38/014* (2013.01); *A61K 38/39* (2013.01)

(58) Field of Classification Search
None
See application file for complete search history.

(56) References Cited

FOREIGN PATENT DOCUMENTS

CN       104161720     * 11/2014

* cited by examiner

*Primary Examiner* — Michael V Meller

(57) ABSTRACT

The present invention aids to correct erectile dysfunction by increasing blood circulation on the skin when applied topically.
This composition is made with all organic food grade ingredients in form of a lotion than when rubbed on the skin, in a time-controlled fashion, is nutrition for the skin.

1 Claim, No Drawings

NON MEDICATED LOTION TO CORRECT ERECTILE DYSFUNCTION

FIELD OF INVENTION

The present invention generally related to compositions and methods for topical enhancement of erectile dysfunction.

BACKGROUND

All food grade ingredients such as peptides, vitamins and skin improving compounds to act locally at the point of application systemically is absorbed into the skin improving blood circulation.

SUMMARY

The present invention generally related to compositions and methods for topical enhancement correcting erectile dysfunction. The composition is made of organic food grade ingredients with no side effects, it is nutrition for the skin.

DETAILED DESCRIPTION

The present invention generally related to compositions and methods for topical enhancement of erectile dysfunction. The invention claimed here to solve male erectile dysfunction problem. When the lotion is applied to skin it enhances blood circulation. The increased blood circulation aids in correcting, erectile dysfunction. The claimed invention differs from what currently exists Combining natural ingredients in the proper sequence and temperature produces a very effective lotion. Other lotions don't work well due to the use of skin irritating compounds with chemical ingredients. By using all natural biodegradable ingredients this lotion improves on all others it helps to heal irritation in a natural way.

This composition made with organic food grade ingredients in form of lotion that rubbed onto the skin in a time-controlled fashion is nutrition for the skin.

The Version of the Invention Discussed Here Includes the Following Components:
1 Coconut oil
2 Collagen
3 Glycerin
4 Pumpkin Seed oil
5 Apple Cider vinegar
6 Gelatin
7 Vitamin E
8 Sodium Citrate
9 Citric Acid
10 Vanilla extract
11 L-Arginine
12 Ascorbic Acid
13 Lecithin
14 Coconut Milk
15 Tiger Nut Milk
16 Ylang-yang extract
17 Ginseng extract
18 Aloe Vera juice
19 Saw Palmetto
20 Vitamin K
21 Agave Tequila
22 See Buckhorn oil
23 Lavender extract
24 Clove essential oil
25 Orange or Lemon essential oil Relationship. Between the Components:
1 Coconut Oil: Moisturizers the Skin
2 Collagen: Makes the skin elastic and firm, it reduces inflammation
3 Glycerin: By lubricating it aids erectile dysfunction problems
4 Pumpkin Seed. Oil: Improves blood flow, helps muscles to relax
5 Apple Cider vinegar: As a disinfectant, cleans skin
6 Gelatin: Provides strength and structure for tissues
7 Vitamin E: Improves blood flow
8 Sodium Citrate: Improves circulation and acts as a preservative
9 Citric Acid: Improves energy production to the muscles
10 Vanilla Extract: Increases sexual desire, also adds flavor
11 L-Arginine: Increases blood circulation in the vessels achieving a stronger erection
12 Ascorbic Acid: increase testosterone levels
13 Lecithin: Smooth and moisturize skin
14 Coconut Milk: Anti-inflammatory properties, it contains antioxidants
15 Tiger Nut milk: Act as an aphrodisiac, helps fight infections
16 Ylang-ylang Extract: Enhances libido, reduces inflammation
17 Ginseng Oil: Helps correct erectile dysfunction
18 Aloe Vera Juice: A natural moisturizer heals skin
19 Saw Palmetto: Influence sex hormone levers
20 Vitamin K: help with erectile dysfunction
21 Agave Tequila: Reduces inflammation, improves skin absorption
22 Sea Buckhorn Oil: Promotes skin elasticity and prevents growth of bacteria
23 Lavender Extract Reduces inflammation, is anti-microbial and anti-fungal, also good aroma
24 Clove essential oil: Anti-bacterial and anti-fugal properties, also good aroma
25 Lemon or Orange essential oil: Anti-bacterial and anti-fugal properties, also good aroma The Components Weight:

| | | | |
|---|---|---|---|
| # 1 | Coconut oil | 71.60 g | 7.98 wt % |
| # 2 | Collagen | 34.00 g | 3.79 wt % |
| # 3 | Glycerin | 34.70 g | 3.86 wt % |
| # 4 | Pumpkin Seed oil | 101.40 g | 11.30 wt % |
| # 5 | Apple Cider vinegar | 124.00 g | 13.81 wt % |
| # 6 | Gelatin | 13.00 g | 1.45 wt % |
| # 7 | Vitamin E | 9.10 g | 1.01 wt % |
| # 8 | Sodium Citrate | 6.80 g | 0.76 wt % |
| # 9 | Citric Acid | 9.90 g | 1.10 wt % |
| # 10 | Vanilla extract | 6.70 g | 0.74 wt % |
| # 11 | L-Arginine | 107.40 g | 11.96 wt % |
| # 12 | Ascorbic Acid | 11.60 g | 1.29 wt % |
| # 13 | Lecithin | 38.70 g | 4.31 wt % |
| # 14 | Coconut Milk | 78.00 g | 8.69 wt % |
| # 15 | Tiger Nut Milk | 70.00 g | 7.80 wt % |
| # 16 | Ylang-ylang extract | 0.50 g | 0.05 wt % |
| # 17 | Ginseng extract | 4.00 g | 0.44 wt % |
| # 18 | Aloe Vera juice | 115.00 g | 12.81 wt % |
| # 19 | Saw Palmetto | 4.40 g | 0.49 wt % |
| # 20 | Vitamin K | 4.40 g | 0.49 wt % |
| # 21 | Agave Tequila | 25.00 g | 2.78 wt % |
| # 22 | See Buckhorn oil | 1.00 g | 0.11 wt % |
| # 23 | Lavender extract | 26.30 g | 2.93 wt % |

-continued

| # 24 | Clove essential oil | 0.50 g | 0.05 wt % |
| # 25 | Orange or Lemon essential oil | 26.30 g | 2.93 wt % |
| | Total: | 898.00 g | 100.00 wt % |

How the Invention Works

This lotion works by enhancing blood circulation on the skin of the genital areas, relaxing the muscles and helping an erection that facilitates the experience to temporarily correct for Erectile Dysfunction It helps achieve this without the use of harsh chemicals and no side effects How to Make the Invention This lotion is made in a clean sterile environment to prevent contamination using only safe natural food grade organics products.

Mixing the ingredients is required following the proper steps to accomplish the desired consistency at the proper temperatures and blended to avoid clumping:

Phase 1—Components 1 through 7 blended at temperature of 98° C. at low speed for 40 sec.

Phase 2—Add components 8 through 9 blended at temperature of 88° C., start at low speed and gradually to high speed for 35 sec.

Phase 3—Add components 10 through 13 blended at temperature of 82° C., start at low speed and gradually to high speed for 35 sec.

Phase 4—Add components 14 through 17 blended at temperature of 66° C., start at low speed and gradually to high speed for 35 sec.

Phase 5—Add components 18 through 22 blended at temperature of 32° C., start at low speed and gradually to high speed for 35 sec.

Phase 6—Add aroma of choice:
Components 23 with 24 blended at temperature of 24° C. at low speed for 40 sec.
or
Components. 24 with 25 blended at temperature of 24° C. at low speed for 40 sec.

Components 1 through 22 are necessary.

Components 23 through 25 can be substituted for a different flavor.

Higher concentrations of components 4, 7, 10, 11, 15, 16, 17, 19 and 20 can be used to increase the potency in the future.

The elements are listed in the proper mixing sequence to create a good consistency.

Elements 1 through 22 may be substituted or reconfigured in the future for better effectiveness.

The solution is poured in individual sterile jars with lids and seal.

Proper labels are added listing the ingredients, directions and contact information for the consumer.

Store at room temperature 12 C-27 C (55 F-80 F)

How to Use the Invention

This lotion enhances blood circulation on the skin, it should be applied on the genital areas and rubbed in for better absorption.

Additionally: Also it can be applied to the face, neck, hands and arms to hydrate the skin and produce a radiant look, wrinkle free when applied daily.

The invention claimed is:

1. A method for treating erectile dysfunction in a human in need thereof consisting essentially of administering to the human in need thereof 11.96 wt. % L-Arginine, 11.30 wt. % Pumpkin Seed Oil, 3.86 wt. % Glycerin, 1.01 wt. % Vitamin E, 1.29 wt. % Ascorbic Acid, 0.74 wt. % Vanilla Extract, 0.05 wt. % Ylang—Ylang Extract, 0.44 wt. % Ginseng Extract, 0.49 wt. % Saw Palmetto, 0.49 wt. % Vitamin K, 0.05 wt. % Clove Essential Oil, 7.98 wt. % Coconut Oil, 3.79 wt. % Collagen, 1.45 wt. % Gelatin, 12.81 wt. % Aloe Vera Juice, 4.31 wt. % Lecithin, 8.69 wt. % Coconut Milk, 7.80 wt. % Tiger Nut Milk, 0.11 wt. % Sea Buckhorn Oil, 2.93 wt. % Orange essential oil, 2.93 wt. % Lemon Essential Oil, 2.93 wt. % Lavender Extract, 2.78 wt. % Agave Tequila and 13.81 wt. % Apple Cider Vinegar to effectively treat the erectile dysfunction in the human in need thereof.

* * * * *